United States Patent [19]

Caspari

[11] Patent Number: 4,679,552
[45] Date of Patent: Jul. 14, 1987

[54] DRAPE FOR ARTHROSCOPIC SURGERY

[75] Inventor: Richard B. Caspari, Maidens, Va.

[73] Assignee: Chattanooga Corporation, Chattanooga, Tenn.

[21] Appl. No.: 788,784

[22] Filed: Oct. 18, 1985

[51] Int. Cl.⁴ .......................... A61F 5/04; A61F 13/00
[52] U.S. Cl. .............................. 128/132 D; 128/84 R
[58] Field of Search ................... 128/132 D, 75, 84 R, 128/87 R, 87 C, 69, 77, 78

[56] References Cited

U.S. PATENT DOCUMENTS

| | | | |
|---|---|---|---|
| 1,149,341 | 8/1915 | Carlson | 128/84 C |
| 2,723,663 | 11/1955 | Davis . | |
| 2,817,333 | 12/1957 | Cole | 128/84 R |
| 3,039,459 | 6/1962 | Scholl . | |
| 3,297,026 | 1/1967 | Van Pelt . | |
| 3,477,428 | 11/1969 | Hare . | |
| 3,572,327 | 3/1971 | Beard et al. . | |
| 3,780,731 | 12/1973 | Quello . | |
| 3,867,930 | 2/1975 | Brown . | |
| 3,934,582 | 1/1976 | Gorrig | 128/157 |
| 4,146,021 | 3/1979 | Brosseau et al. . | |

Primary Examiner—Robert A. Hafer
Assistant Examiner—Kathleen J. D'Arrigo
Attorney, Agent, or Firm—Bell, Seltzer, Park & Gibson

[57] ABSTRACT

A surgical drape is disclosed which is adapted for protectively covering a limb of a patient during arthroscopic surgery, and while placing the limb in traction. The drape comprises a tubular sleeve, a pair of elongate traction strips mounted on the inside of the sleeve, and strap means overlying the outside of the sleeve and having opposite ends attached through the sleeve to respective ones of the traction strips. Also, a wrap is provided for encircling the sleeve when the sleeve is mounted on the limb of patient to circumferentially bind the tubular sleeve upon the limb. When the tubular sleeve is thus mounted upon the limb, a traction force may be applied to the strap, which results in the force being applied to the limb along the elongate contact area between the traction strips and the limb, and such that the force is distributed over a broad area so as to avoid injury to the limb. A method of fabricating the sleeve is also disclosed.

9 Claims, 8 Drawing Figures

U.S. Patent   Jul. 14, 1987   Sheet 1 of 2   4,679,552
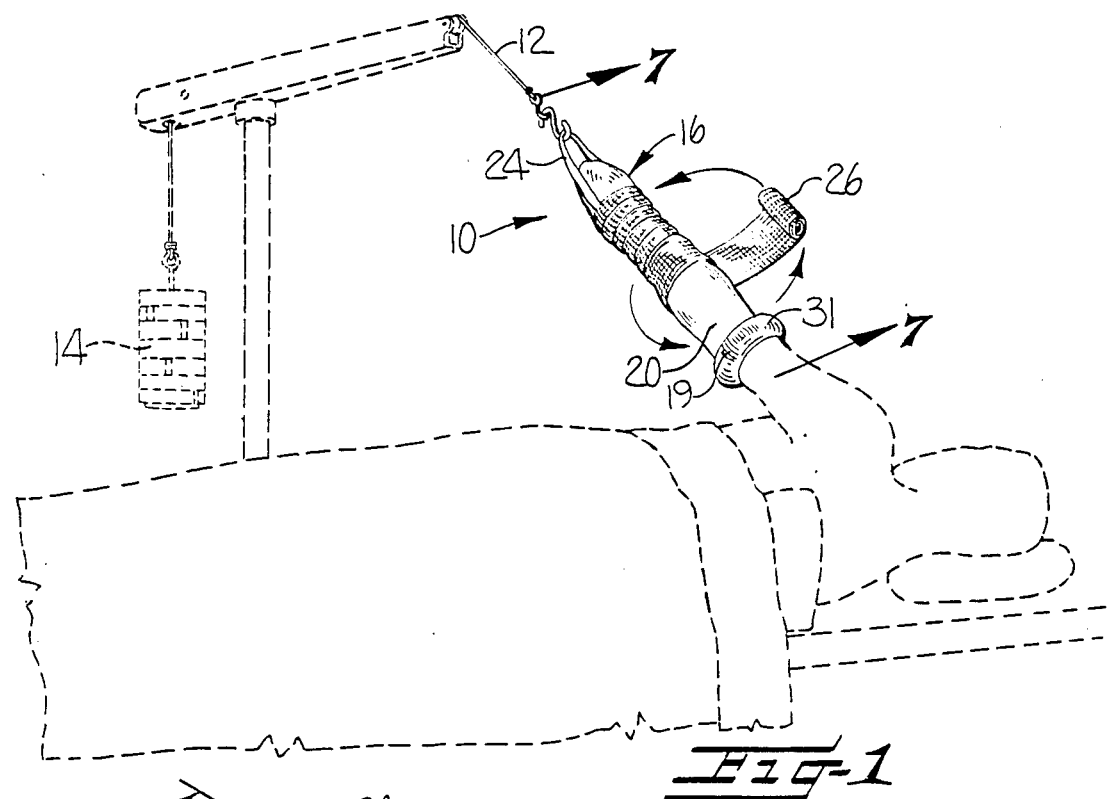
Fig-1
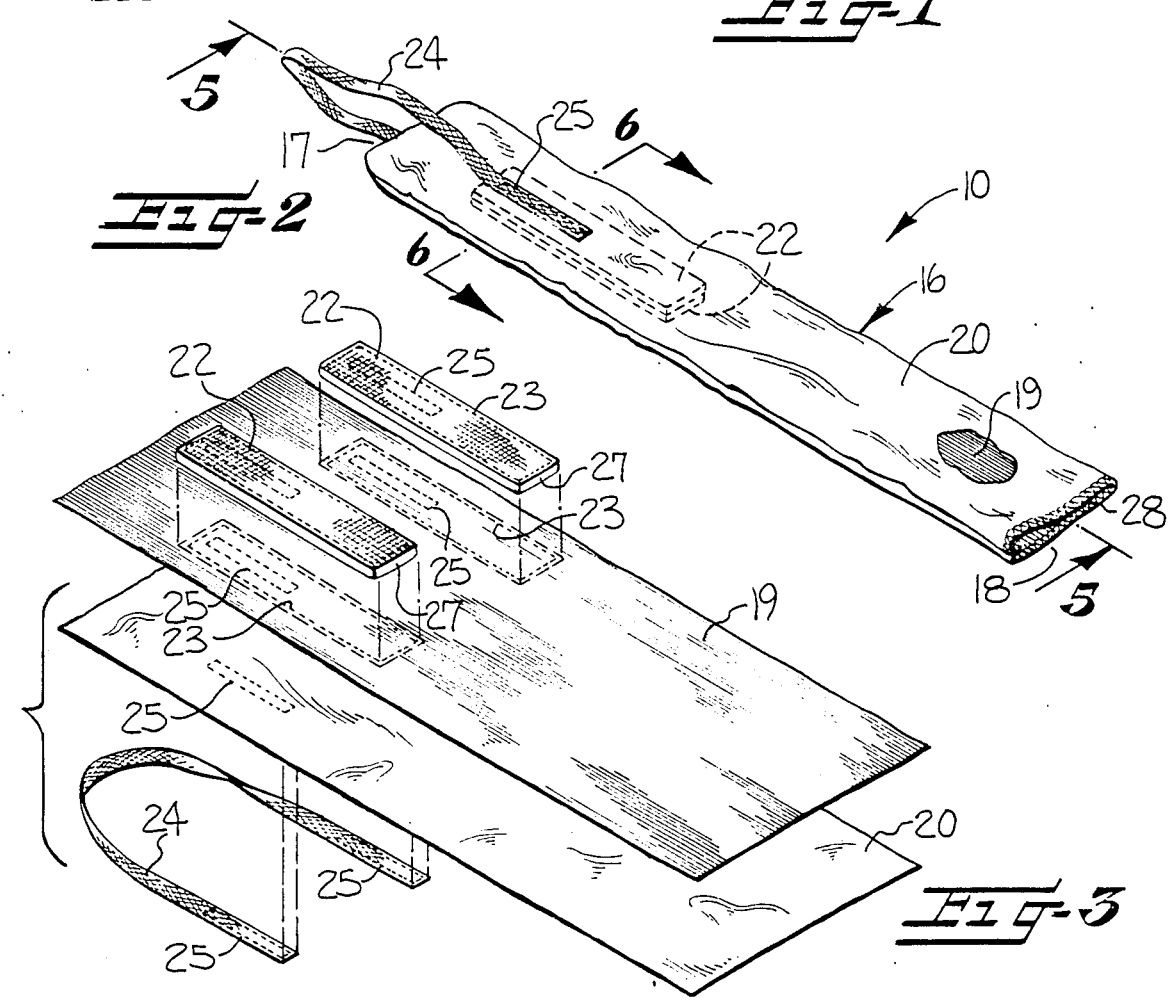
Fig-2
Fig-3

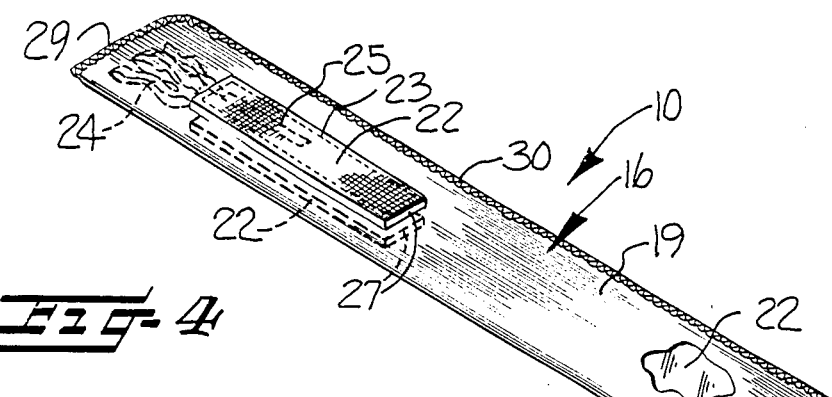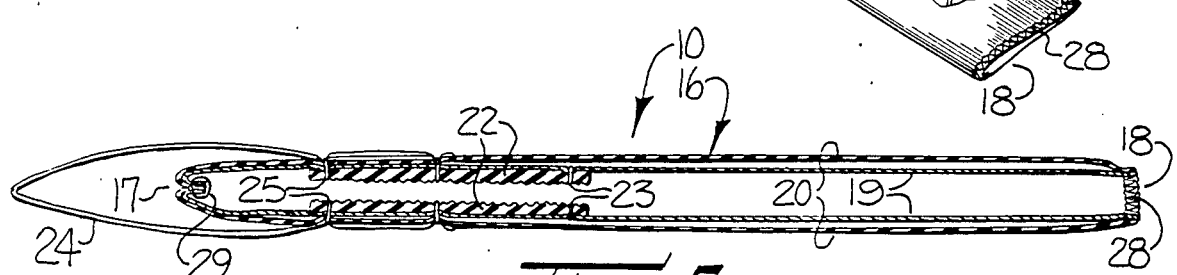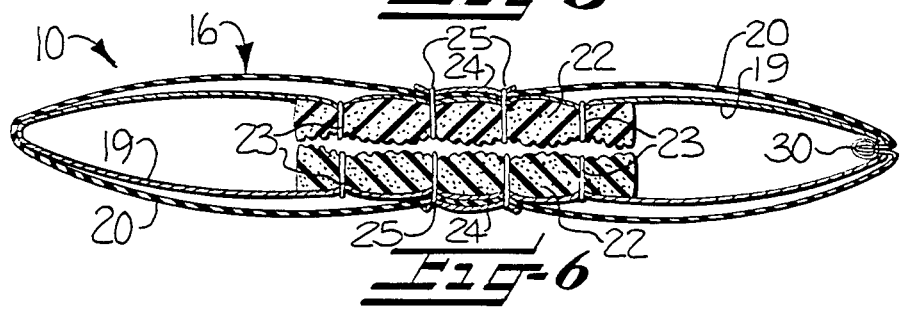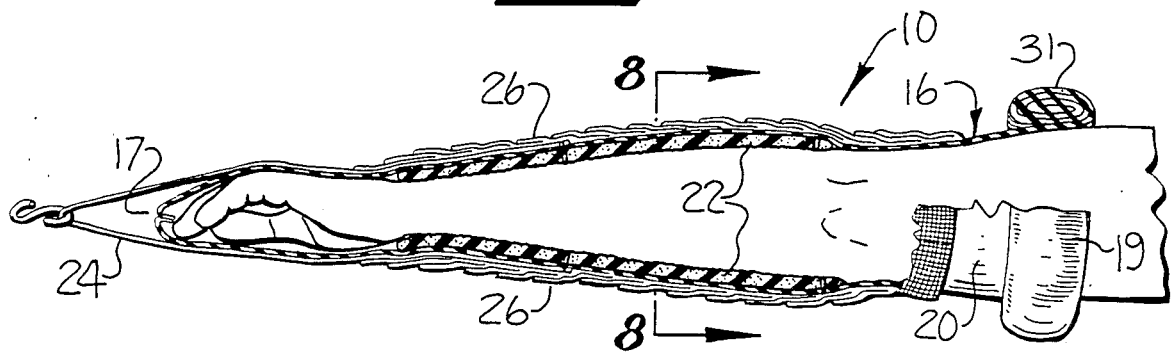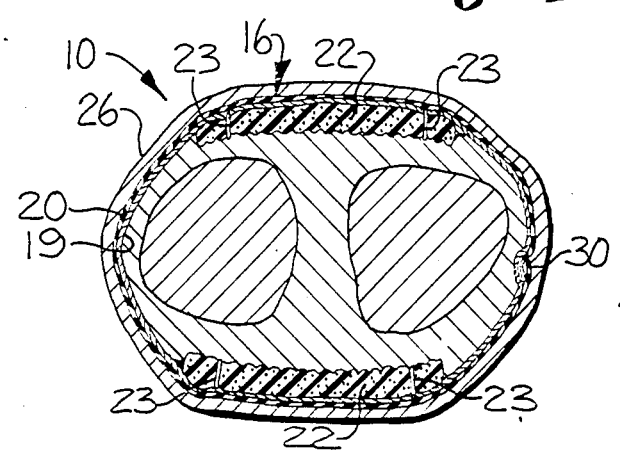

DRAPE FOR ARTHROSCOPIC SURGERY

The present invention relates to a surgical drape adapted for protectively covering a limb of a patient during arthroscopic surgery or the like, and while placing the limb in traction.

Arthroscopic shoulder surgery involves a procedure wherein the arm is placed under a traction force of about 12-15 pounds. A first portal is then formed in the area of the shoulder for inserting the arthroscopic tube wherein the interior of the shoulder joint may be viewed by the surgeon, and a second portal is formed for the surgical instrument. It is also conventional to enclose the arm in a protective drape, which comprises a tubular knit cotton stockinette and a surrounding waterproof latex outer sleeve. The stockinette and sleeve are initially placed over the arm of the patient, and a traction band is then placed about the wrist so as to overlie the stockinette and sleeve. A traction cord is then attached to the band for applying the necessary traction to the arm.

A major problem associated with the prior drape as described above, is the fact that the application of the traction to the wrist could cause injury to the wrist. It is accordingly an object of the present invention to provide a surgical drape for arthroscopic surgery of the described type and which avoids the problem of wrist injury resulting from the applied traction force.

It is also an object of the present invention to provide a convenient and efficient method of fabricating a drape of the described type.

These and other objects and advantages of the present invention are achieved in the embodiment illustrated herein by the provision of a surgical drape which comprises a tubular sleeve of flexible sheet material, with the sleeve being adapted to receive at least a substantial portion of the length of the limb of the patient. Elongate traction pad means is mounted within the tubular sleeve so as to extend along a substantial portion of the length of the patient's limb which is received in the sleeve, and such that portions of the pad means are adapted to extend along opposite sides of the limb. Strap means is also provided which overlies the outside of the tubular sleeve and has opposite ends which are attached through the sleeve to the traction strip means. Also, wrap means is provided for encircling the sleeve when the sleeve is mounted on the limb of a patient to circumferentially bind the tubular sleeve upon the limb. By this arrangement, a traction force may be applied to the strap means, which results in the traction force being applied to the limb, and with the force being distributed along the elongate contact area between the traction pad means and the intermediate limb.

In a preferred embodiment, the traction pad means is composed of a resilient rubber-like material, which is adapted to frictionally engage the limb of the patient. Also, the tubular sleeve preferably comprises an inner layer of relatively soft textile material, such as knit stockinette, and an outer layer of moisture impermeable sheet material, such as a thin sheet of latex.

The sleeve as described above is fabricated by a method which includes the steps of providing a generally rectangular sheet of material, and joining the traction pad means to one side of the sheet. The opposite ends of the strap means are placed on the other side of the sheet, and joined to the traction pad means through the sheet. The sheet is then folded upon itself along its longitudinal centerline, and the overlying longitudinal edges are joined together to form a sleeve. In a preferred embodiment of the method, the sheet is folded so that the traction pad means is on the outside, and the method includes the further subsequent step of turning the sleeve inside out.

Some of the objects and advantages of the present invention having been stated, others will appear as the description proceeds when taken in conjunction with the accompanying drawings, in which FIG. 1 is a somewhat schematic perspective view of a surgical drape which embodies the features of the present invention, and with the drape applied to the arm of a patient positioned for arthroscopic shoulder surgery;

FIG. 2 is a perspective view of the sleeve portion of the drape shown in FIG. 1;

FIGS. 3 and 4 are perspective views illustrating the method of fabricating the drape in accordance with the present invention;

FIG. 5 is a sectional side elevation view taken substantially along the line 5—5 of FIG. 2;

FIG. 6 is a sectional end view taken substantially along the line 6—6 of FIG. 2;

FIG. 7 is a sectional view of the drape applied to the arm of a patient, and taken substantially along the line 7—7 of FIG. 1; and FIG. 8 is a sectional end view taken substantially along the line 8—8 of FIG. 7.

Referring more particularly to the drawings, FIG. 1 schematically illustrates a patient positioned on a surgical table in a position suitable for arthroscopic shoulder surgery, and with the left arm of the patient having a drape 10 applied thereto which embodies the features of the present invention. As will become apparent, the drape 10 serves to protectively cover the arm, and it also serves to place the arm under traction when connected to a cable 12 and depending weight 14 in the illustrated manner.

The drape 10 comprises a tubular sleeve 16 which is closed at one end 17 and open at the other end 18. The sleeve is composed of an inner layer 19 of relatively soft textile material, such as a knit stockinette of cotton or other hydrophilic fiber, and an outer layer 20 of a moisture impermeable sheet material, such as a thin sheet of latex. Traction pad means in the form of a pair of elongate traction strips 22 is mounted within the tubular sleeve, with the strips extending in opposing parallel relation to each other along the length direction of the sleeve. The strips 22 are generally rectangular in outline, and are disposed side by side in the widthwise direction of the sleeve. The strips are thus adapted to extend along opposite sides of the forearm of the patient in the manner best seen in FIGS. 7 and 8. The strips also have a length which is preferably sufficient to reach substantially between the wrist area and elbow area, and they preferably are composed of a resilient rubber-like material, such as foam rubber, which is adapted to frictionally engage the arm of the patient in the manner further described below. If desired, the strips 22 may include a laminated fabric backing (not shown) which is disposed adjacent the sheet 19 for added strength. Preferably, the strips are joined to the sheet by stitching 23, note FIG. 6.

The surgical drape 10 further includes a looped strap 24 which is positioned to overlie the outside of the closed end 17 of the tubular sleeve, with opposite ends of the strap being attached through the sleeve to respective ones of the traction strips 22. This attachment may conveniently be effected by stitching 25 as best seen in FIG. 6.

The drape 10 also includes a flexible wrap 26 for encircling the tubular sleeve when the sleeve is mounted on the arm of the patient, to circumferentially bind the tubular sleeve upon the arm in the manner best seen in FIG. 7. The wrap 26 may comprise any suitable flexible bandage-like material, such as "Coban" self-adherent wrap manufactured by The 3M Company of St. Paul, Minn.

FIGS. 3 and 4 illustrate the manner in which the tubular sleeve 16 of the drape may be fabricated in accordance with the present invention. In particular, a rectangular sheet 19 of soft absorbent textile material and a correspondingly sized thin sheet 20 of elastic latex are prepared. The two traction strips 22 are then placed upon the textile sheet 19, with the elongate dimension of the strips being aligned with the longitudinal direction of the sheet and with the strips having transversely aligned ends 27 which lie generally along the transverse centerline of the sheet 19. Also, the strips 22 are positioned so as to be substantially equally spaced from the longitudinal centerline of the sheet, and the strips are joined to the sheet 19 by stitching 23. Next, the two sheets 19 and 20 are disposed in overlying relation, and the ends of the strap 24 are joined through the two sheets to respective ones of the traction strips 22 by stitching 25. The two aligned edges of the sheets which will form the open end 18 of the sleeve are then joined by overedge stitching 28, and the resulting product is then folded along its longitudinal centerline with the textile sheet 19 and traction strips 22 being on the outside. The aligned edges of the two sheets at the closed end 17 of the sleeve, and the aligned edges along the longitudinal direction, are then joined by overedge stitching 29, 30 respectively, to produce the intermediate product as illustrated in FIG. 4. It will also be seen that the strap 24 is on the inside of the intermediate product. The intermediate product is then turned inside out to produce the tubular sleeve 16 as shown in FIG. 2. As a result, the overedge stitching 29, 30 is disposed on the inside of the sleeve, note FIGS. 5 and 6. If desired, the sleeve may be rolled from the open end 18 toward the closed end 17 into a doughnut configuration (not shown) to facilitate packaging and subsequent application of the sleeve to the limb of a patient.

Where the tubular sleeve 16 is rolled into a doughnut configuration, it is applied to the arm by unrolling the sleeve along the length of the arm, and any excess length may be maintained in its doughnut configuration, as indicated at 31 in FIG. 1. The wrap 26 is then applied by encircling the sleeve to circumferentially bind the sleeve upon the limb, and finally, an S-hook 32 is employed to interconnect the strap to the traction cable 12 and weight 14 so that the arm of the patient is placed under the desired traction force. As will be understood, the traction force is applied to the arm primarily through the traction strips 22, and in view of their elongated configuration, the traction force is distributed along an elongate contact area which extends substantially between the wrist and elbow on both the top and the bottom of the forearm. Thus the risk of injury resulting from the application of the force is minimized.

In the drawings and specification, there has been set forth a preferred embodiment of the invention, and although specific terms are employed, they are used in a generic and descriptive sense only and not for purposes of limitation.

That which is claimed is:

1. A surgical drape adapted for protectively covering a limb of a patient during arthroscopic surgery or the like and while applying traction to the limb, and comprising a tubular sleeve of flexible sheet material, with said sleeve having a length adapted to receive at least a substantial portion of the length of the limb of the patient, traction pad means mounted within a portion of said tubular sleeve, with said pad means having a length dimension sufficient to extend along a substantial portion of the length of the limb, and having portions thereof which are adapted to lie along opposite sides of the limb of the patient which is received in the sleeve, strap means positioned on the outside of said tubular sleeve and having opposite ends attached through said sleeve to said traction pad means, and wrap means for encircling the sleeve when the limb of a patient is received therein to circumferentially bind the tubular sleeve upon the limb, and such that a traction force may be applied to said strap means which results in the traction force being applied to the limb which is distributed along the elongate contact area beween said traction pad means and the intermediate limb.

2. The surgical drape as defined in claim 1 wherein said traction pad means is composed of a resilient rubber-like material which is adapted to frictionally engage the limb of the patient.

3. The surgical drape as defined in claim 2 wherein said tubular sleeve comprises an inner layer of relatively soft textile material and an outer protective layer of moisture impermeable sheet material.

4. The surgical drape as defined in claim 3 wherein said inner layer of said tubular sleeve comprises a knit cotton fabric, and said outer layer comprises a thin sheet of latex.

5. The surgical drape as defined in claim 3 wherein said traction pad means comprises a pair of elongate traction strips, with the strips being disposed side by side in the widthwise direction of said sleeve and so as to extend in opposing parallel relation along the length direction of the sleeve.

6. The surgical drape as defined in claim 5 wherein said strap means comprises a unitary strap which overlies one end of said sleeve, and wherein said one end is closed.

7. A surgical drape adapted for protectively covering a limb of a patient during arthroscopic surgery or the like and while applying traction to the limb, and comprising a tubular sleeve composed of an inner layer of relatively soft textile material and an outer protective layer of moisture impermeable material, with said sleeve having a length adapted to receive at least a substantial portion of the length of the limb of the patient, a pair of elongate traction strips mounted within said tubular sleeve, with said strips each having a length dimension sufficient to extend along a substantial portion of the length of the limb, and with said strips being separated in the widthwise direction so as to be adapted to lie along opposite sides of the limb of the patient which is received in the sleeve, strap means positioned on the outside of said tubular sleeve and having opposite ends attached through said sleeve to respective ones of said traction strips, and wrap means for encircling the sleeve when the limb of a patient is received therein to circumferentially bind the tubular sleeve upon the limb, and such that a traction force may be applied to said strap means which results in the traction force being applied to the limb which is distributed along the elongate contact area beween said traction strips and the intermediate limb.

8. The surgical drape as defined in claim 7 wherein said sleeve is closed at one end, and comprises a folded seam along one longitudinal side edge and a sewn seam along said one closed end and the other longitudinal side edge.

9. The surgical drape as defined in claim 7 wherein said pair of elongate traction strips are each joined to said inner layer by stitching, and wherein the ends of said strap member are joined to said traction strips by stitching which extends through both said inner and outer layers.

* * * * *